(12) United States Patent
Kosa et al.

(10) Patent No.: US 6,999,220 B2
(45) Date of Patent: Feb. 14, 2006

(54) DEVICE EXHIBITING PHOTO-INDUCED DICHROISM FOR ADAPTIVE ANTI-GLARE VISION PROTECTION

(75) Inventors: Tamas Kosa, Kent, OH (US); Peter Palffy-Muhoray, Kent, OH (US); Bahman Taheri, Hudson, OH (US)

(73) Assignee: AlphaMicron, Inc., Kent, OH (US)

( * ) Notice: Subject to any disclaimer, the term of this patent is extended or adjusted under 35 U.S.C. 154(b) by 245 days.

(21) Appl. No.: 10/702,343

(22) Filed: Nov. 6, 2003

(65) Prior Publication Data

US 2004/0090570 A1  May 13, 2004

Related U.S. Application Data

(63) Continuation of application No. 09/678,597, filed on Oct. 3, 2000, now Pat. No. 6,690,495.

(51) Int. Cl.
 *G02F 1/1334* (2006.01)
(52) U.S. Cl. ......................... 359/241; 349/86
(58) Field of Classification Search ............... 359/241; 349/86
 See application file for complete search history.

(56) References Cited

U.S. PATENT DOCUMENTS

| | | | |
|---|---|---|---|
| 2,319,816 A | 5/1943 | Land | 88/65 |
| 3,653,863 A | 4/1972 | Araujo et al. | 65/30 |
| 4,039,254 A | 8/1977 | Harsch | 350/160 |
| 4,279,474 A | 7/1981 | Belgorod | 350/331 |
| 4,549,894 A | 10/1985 | Araujo et al. | 65/30.11 |
| 4,685,771 A | 8/1987 | West et al. | 350/347 |
| 4,688,900 A | 8/1987 | Doane et al. | 350/347 |
| 4,728,173 A | 3/1988 | Toth | 350/332 |
| 4,756,605 A | 7/1988 | Okada et al. | 350/347 |
| 5,067,795 A | 11/1991 | Senatore et al. | 359/84 |

(Continued)

FOREIGN PATENT DOCUMENTS

GB    2 169 417 A    7/1986

(Continued)

OTHER PUBLICATIONS

G. W. Gray, *Dyestuffs And Liquid Crystals*, pp. 47-51 (Feb. 1980), Chimia 34 Nr. 2.

(Continued)

*Primary Examiner*—Scott J. Sugarman
*Assistant Examiner*—Richard Hanig
(74) *Attorney, Agent, or Firm*—Renner, Kenner, Greive, Bobak, Taylor & Weber

(57) ABSTRACT

A device (100, 140, 150) for differentially absorbing light, depending on the state of linear polarization of the light, is disclosed. This polarizing effect is induced and controllable by the level of ambient light impinging on the device. The device (100, 140) may be used as an anti-glare vision protection device which selectively absorbs specularly reflected sunlight in brightly lit environments while permitting all light to pass in dimly lit environments. The device (100) includes a carrying medium which may be a film (142) or opposed substrates (112) that are sealed. A film or the opposed substrates carry a mixture (120) of fluid material (124) and photochromic dyestuffs (122), wherein the photochromic material is activated upon the detection of ultraviolet light so as to absorb some of the light and wherein the energization of the photochromic material effects the material so as to simultaneously selectively absorb the specularly reflected sunlight. The material (124) may be any fluid that dissolves the photochromic dyestuff material (122). The fluid is preferably a liquid crystal material such as nematic or chiral nematic. Alternatively, the material (124) may be a polymer liquid crystal. The device (150) may allow for electrical control of the absorptive properties.

14 Claims, 6 Drawing Sheets

U.S. PATENT DOCUMENTS

| | | | |
|---|---|---|---|
| 5,155,607 A * | 10/1992 | Inoue et al. | 349/89 |
| 5,202,063 A | 4/1993 | Andrews et al. | 264/4.6 |
| 5,552,841 A | 9/1996 | Gallorini et al. | 351/49 |
| 5,608,033 A | 3/1997 | Nihira et al. | 528/353 |
| 5,608,567 A | 3/1997 | Grupp | 359/275 |
| 5,615,032 A | 3/1997 | Kalmanash et al. | 349/165 |

FOREIGN PATENT DOCUMENTS

| | | |
|---|---|---|
| JP | 61057935 | 3/1986 |
| JP | 5297417 A | 11/1993 |
| JP | 10031208 | 2/1998 |
| WO | WO 98/19207 | 5/1988 |
| WO | WO 0019252 | 4/2000 |
| WO | WO 00/77559 | 12/2000 |

OTHER PUBLICATIONS

International Search Report dated Jun. 5, 2003.

* cited by examiner

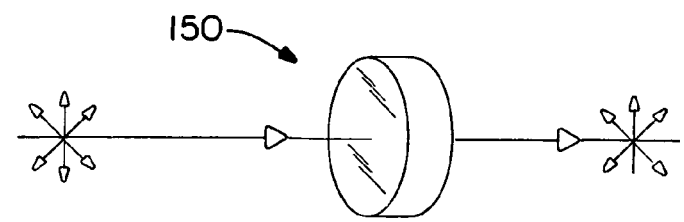
FIG.-13A
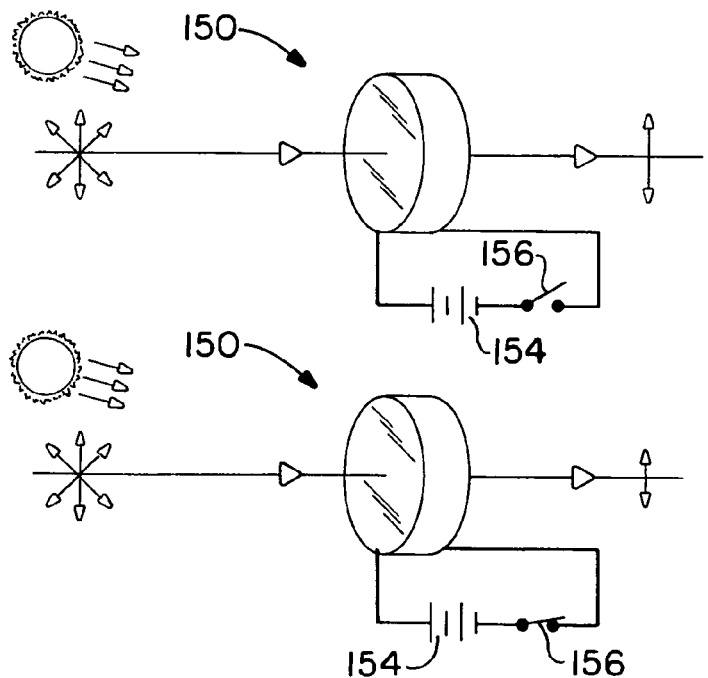
FIG.-13B
FIG.-13C
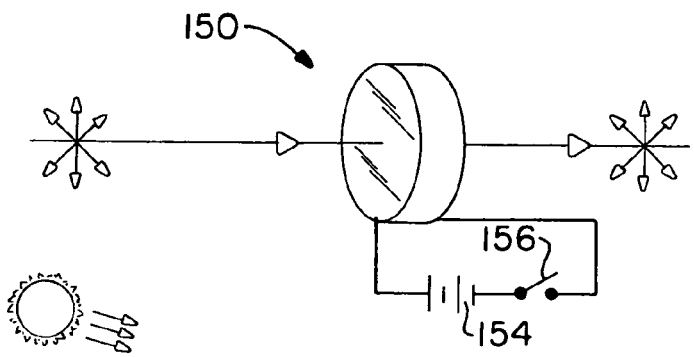
FIG.-14A
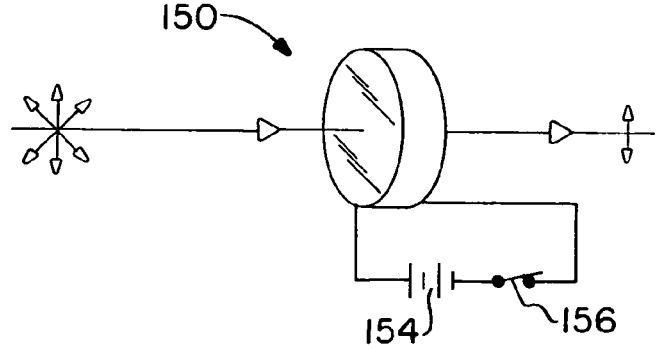
FIG.-14B

DEVICE EXHIBITING PHOTO-INDUCED DICHROISM FOR ADAPTIVE ANTI-GLARE VISION PROTECTION

CROSS REFERENCE TO RELATED APPLICATION

This is a continuation of patent application Ser. No. 09/678,597, filed October 3, 2000, now U.S. Pat. No. 6,690,495 entitled "Device Exhibiting Photo-Induced Dichroism for Adaptive Anti-Glare Vision Protection."

TECHNICAL FIELD

This invention relates to ophthalmic devices. More particularly, this invention relates to devices that change optical characteristics as a result of exposure to ultraviolet light. Specifically, this invention relates to devices that simultaneously polarize and absorb light depending on the state of linear polarization of the light.

BACKGROUND ART

Coatings and material layers are often applied to optical elements such as ophthalmic lenses, sunglasses, visors, windshields, etc. for controlling the level of light passing through these elements. There are two common types of sunglasses that use such special coatings and materials.

The first type are the "anti-glare" sunglasses. On sunny days, objects in one's field of vision often reflect sunlight specularly. This reflection is far brighter than the diffusely reflected light from the same object, rendering the object difficult to see. These reflections are commonly called "glare." Presently, anti-glare coatings to reduce these undesirable seeing conditions are dichroic. In other words, they preferentially absorb light having a particular plane of linear polarization. The original Polaroid H sheet (U.S. Pat. No. 2,319,816) was a dichroic polarizer. It functions by absorbing (and hence, removing) light with direction of polarization perpendicular to its polarizing axis, and allowing to pass light that has direction of polarization parallel to its polarizing axis. Such coatings perform their anti-glare role because specularly-reflected light is partially linearly polarized and, thus, can be absorbed by a dichroic layer, properly oriented, on the optical element before the wearer's eyes. The diffusely-reflected light is randomly polarized, and so is only very weakly altered by the dichroic coating.

The second type are the "photochromic" sunglasses. Their apparent color (the amount of light they absorb at a particular wavelength or wavelengths) reversibly changes in response to the intensity of light with which they are illuminated. Typically, the photochromic reaction is in response to bright ultraviolet illumination, while the enhanced absorption is at visible wavelengths. These devices rely on a reversible photo induced chemical reaction in which a dye molecule absorbs ultraviolet photons, changes either chemically or conformationally, and the reaction product has an altered absorption characteristic of visible light. These familiar eyeglasses become dark in bright sunlight, and return to clear when indoors in a dimmer environment. These familiar devices have the drawback that the degree to which the absorption changes is controlled entirely by the intensity of ambient light, and not by the wearer.

Anti-glare sunglasses always perform their function. That is, they always differentially absorb light depending on its state of polarization, regardless of whether the effect is desired or not. The wearer of such eyewear frequently must remove the device when the ambient light level becomes dimmer, as when clouds cover the sun or when going indoors in order to see adequately in the dimmer environment. This may even become a safety hazard, as when entering a tunnel while driving on a sunny day.

Photochromic sunglasses only control the level of light transmission when the ambient light level is high, but they offer no protection against glare. Thus, although the amount of light entering the eye is reduced, this reduction alone may not result in clearer vision. Moreover, passive photochromic devices—those that rely solely on the absence or presence of ultraviolet light to change states—are very slow to change states. Typical photochromic sunglasses take ten to fifteen minutes to revert from a dimmed state to a bleached state. Notable prior art, U.S. Pat. No. 4,549,894, describes photochromic glass that regains a transmissivity 1.75 greater than it possesses in the fully darkened state 300 seconds after the activating illumination is removed. A variation on eyewear exhibiting this functionality exists, such as disclosed in U.S. Pat. No. 5,552,841, but it employs electro-optic means of controlling the light transmission in conjunction with electric-eye type devices. Such a device is complicated to manufacture, and still provides no glare protection.

Liquid crystal light shutters have also been executed as light transmission elements for eyewear. Some notable prior art is described in U.S. Pat. No. 4,279,474. In these devices, the electrically controllable birefringence of liquid crystals is exploited by sandwiching them between polarizers. In this execution, the light transmissivity of the eyewear is controlled via an external electrical signal. Often, this signal is slaved to a photo sensor to produce responsive eyewear. A familiar example of this are the "automatic" windows in welding helmets that rapidly darken when an arc is struck, protecting the wearer's vision, as described in U.S. Pat. No. 4,039,254.

U.S. Pat. No. 3,653,863 discloses an optical device capable of reversibly changing from a clear unpolarized state to a darkened polarized state upon exposure to actinic radiation. Such glasses are manufactured from a silicate glass body having elongated silver halide particulars incorporated therein and wherein the orientation of the halide particulars is accomplished by stretching the glass during manufacturing. Although this glass material is effective in its stated purpose, manufacturing of the glass in such a manner is somewhat cumbersome. Moreover, the performance of such a glass is considered to be unacceptable. As noted in the '863 disclosure, transmission in the undarkened state is approximately 77%, whereas in the present invention, transmission in the undarkened or bleached state can be greater than 85%, with the majority of the loss in transmissivity coming from reflective losses that are inherent to any optical device. Other disadvantages of this silver halide glass material are that the performance characteristics are poor and cannot be easily improved upon because when the concentration of silver halide is increased too much, the crystallites become too large and the glass becomes foggy. In the context of eyewear, glass is much heavier than plastic. As such, although the performance properties of the silver halide glass are desirable, the weight of eyewear using glass material is a significant detriment. While the percent polarization of the device described in U.S. Pat. No. 3,653,863 approaches 86%, that of the present reduction-to-practice is about 42% at the 620 nm wavelength. However, the greater percent polarization of the prior art comes at the cost of much greater absorption in the bleached state.

Therefore, there is a need in the art to provide both the capabilities listed in the abovementioned prior art by providing an optical device that differentially absorbs light according to its state of polarization, and performs this task automatically as a function of the intensity of ambient light. This effect is thus referred to as "photo-induced dichroism." There is also a need for this device to be passive and, therefore, impervious to any failure other than being physically broken or having its constituents degrade chemically. If precise active control of the absorption rate is desired, the optical device may be electrically controlled.

DISCLOSURE OF INVENTION

It is thus an object of the present invention to provide a device exhibiting photo-induced dichroism for adaptive anti-glare vision protection.

It is another object of the present invention to provide a device in which a mixture of a fluid material and photochromic dyestuff material exhibits photo-induced dichroism.

It is still another object of the present invention to provide a device, as above, in which the fluid may be an anisotropic liquid crystal material including, but not limited to, such materials as nematic, chiral nematic, and a polymer liquid crystal material.

It is a further object of the present invention to provide a device, as above, in which a mechanism may be provided for holding the mixture in a mechanically stable environment. Such a mechanism may be opposed substrates with the mixture captured therebetween and enclosed by a frame or other sealing adhesive. Another mechanism for holding the mixture may be a phase-separated polymeric film.

It is yet another object of the present invention to provide a device, as above, in which the mixture of a fluid material and photochromic dyestuff material reacts to ultraviolet light exposure to simultaneously absorb and polarize the light. Upon removal of the ultraviolet light, the mixture reverts to its original condition within a relatively short period of time. In other words, the mixture may vary light transmission depending upon the intensity of the ultraviolet light. And the device may perform these functions passively without the need for electrical switching. Or the device may perform these functions actively to precisely control the amount of absorption.

It is yet another object of the present invention to provide a device, as above, in which the substrates may be corrective lenses carried by a frame.

It is still yet another object of the present invention to use the device so that it may be used on windows, camera lenses, and the like.

It is still another object of the present invention to provide a device, as above, wherein the substrates may be provided with an alignment layer so as to uniformly orient the liquid crystal material as desired by the particular end use of the device.

It is yet a further object of the present invention in which each of the opposed substrates may be provided with an electrode to allow for application of an electric field to the mixture. This object allows for selective adjustment of the mixture's light absorbance characteristics by adjusting the electric field applied between the substrates.

It is still yet another object of the present invention to provide a device, as above, in which the substrates, provided with or without electrodes, may be provided with different types of alignment layers to control the operational characteristics of the device.

It is still a further object of the present invention to provide a device, as above, wherein the mixture may be carried by a polymeric film. As such, the invention may incorporate the mixture into a polymeric material using thermal-, solvent-, or polymer ization-induced phase separation. Alternatively, the mixture may include a polymer liquid crystal with embedded photochromic dyestuff material which is then polymerized by known methods. This functions to "lock-in" the dye orientation and attain the desired features of the invention.

It is an additional object of the present invention to provide a device, as above, wherein the polymeric material may be stretched during the phase separation process so as to align the liquid crystal material and photochromic dyestuff material to provide for the linear polarization as discussed above.

It is yet another object of the present invention to apply such a film to a substrate such as a corrective lens or any other end-use application.

The foregoing and other objects of the present invention, which shall become apparent as the detailed description proceeds, are achieved by a device for controlling light transmission, comprising a mixture comprising a fluid material and a photochromic dyestuff material, and a medium for carrying the mixture, wherein the mixture varies between a first condition and a second condition, the first condition letting substantially all light pass through the mixture, and the second condition absorbing light passing through the mixture.

Other aspects of the present invention are attained by a device for exhibiting variable transparency, comprising a pair of opposed substrates positioned adjacent one another and having a gap therebetween, and a light sensitive material disposed in the gap, the material selectively absorbing light when exposed to ultraviolet light, and the material allowing substantial transmission of light when exposure to ultraviolet light is removed.

Still another object of the present invention is attained by a device for controlling light transmission, comprising a film carrying a mixture of at least a nematic liquid crystal material and a photochromic dyestuff material, the film selectively polarizing and absorbing light when exposed to ultraviolet light and the material allowing substantial transmission of light when exposure to ultraviolet light is removed.

A preferred device, incorporating the concepts of the present invention, is shown by way of example in the accompanying drawings without attempting to show all the various forms and modifications in which the invention might be embodied, the invention being measured by the appended claims and not by the details of the specification.

BRIEF DESCRIPTION OF THE DRAWINGS

For a complete understanding of the objects, techniques and structure of the invention, reference should be made to the following detailed description and accompanying drawings, wherein:

FIGS. 13A–C show an alternative electrically controlled device in various states of operation; and FIGS. 14A-B show another alternative electrically controlled device in various states of operation.

PREFERRED EMBODIMENT FOR CARRYING OUT THE INVENTION

Figure 1:
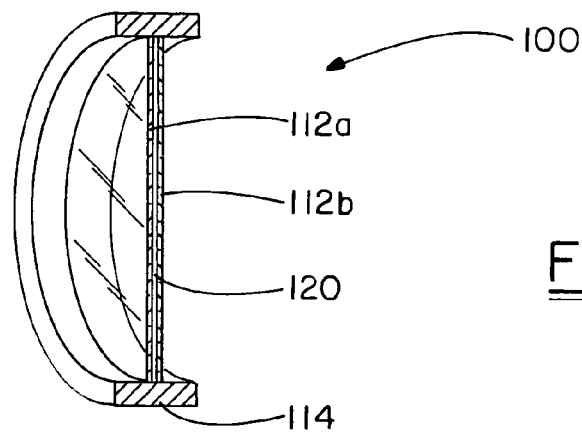
FIG. 1 is a cross-sectional view of the device according to one embodiment of the present invention.

A device exhibiting photo-induced dichroism for adaptive anti-glare vision protection made in accordance with the concepts of the present invention is indicated generally by the numeral 100 in the accompanying drawings and is best seen generally in FIG. 1. The primary components of the device are a pair of opposed substrates 112 and a carrying medium such as a frame or sealant 114. The carrying device could also be a holder, an adhesive material, or the like. The substrates 112, wherein each substrate is identified by a separate alphabetic suffix, such as 112a and 112b, are opposed with a gap therebetween and may be constructed out of glass, plastic, or other transparent material. The substrates 112a, 112b may be rigid or flexible, flat or curved, depending upon the end-use application of the device 100.

Figure 2:
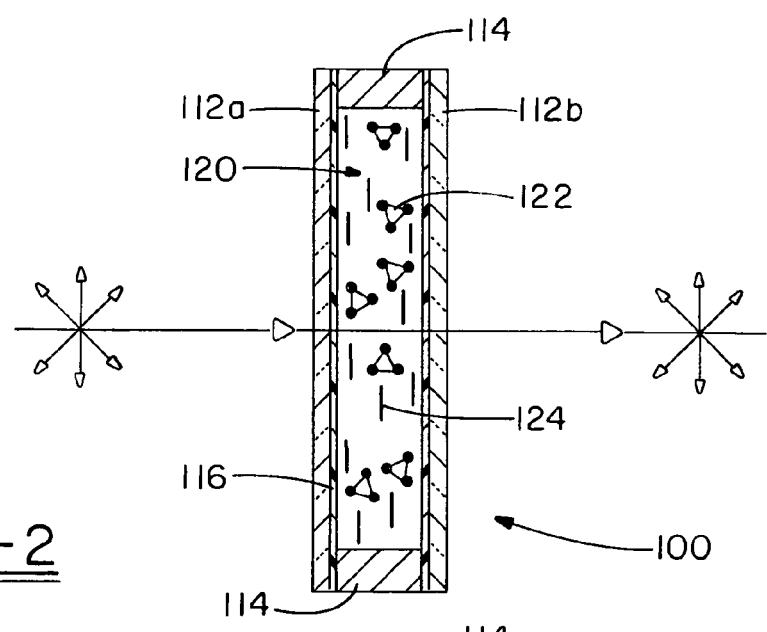
FIG. 2 is a schematic representation of the device in a first condition.
Figure 3:
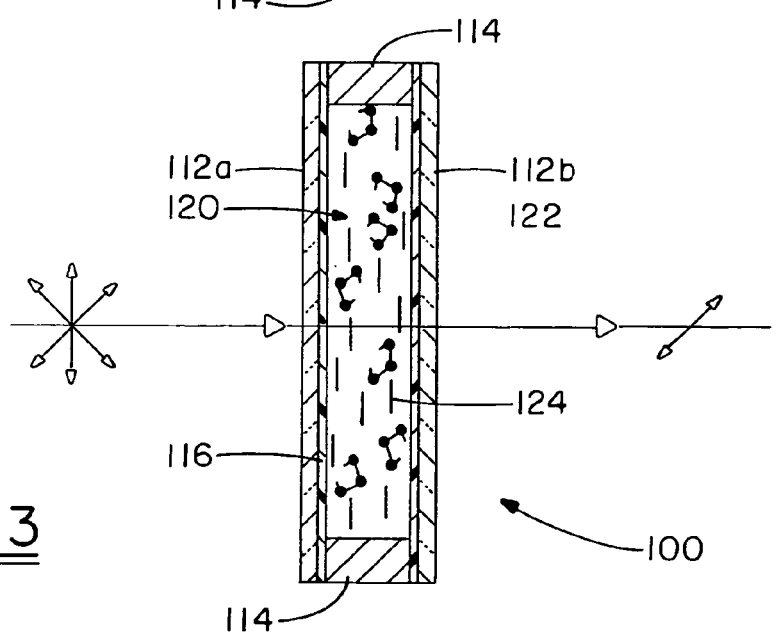
FIG. 3 shows the same device in a second condition.

As best seen in FIGS. 2 and 3, the facing surfaces of the substrates 112a and 112b may be provided with an alignment layer 116. As will be discussed in detail below, use or nonuse of alignment layers is dependent upon the operational characteristics desired by the end-user. As such, the devices disclosed herein may be provided without alignment layers, an alignment layer on just one of the substrates, or alignment layers on each of the substrates. In a passive device embodiment, the alignment layer 116 comprises a thin layer of polyamide which has been deposited in a manner well-known in the art and unidirectionally rubbed in the customary manner for producing liquid crystal cells. The direction of rubbing determines the direction of the linear polarization state that is preferentially absorbed.

A mixture, generally designated by the numeral 120, is disposed between the substrates 112a and 112b and is in contact with the alignment layers 116. The mixture is contained between the substrates by the carrying medium 114. The mixture 120 includes a photosensitive or a photochromic dyestuff material 122 and a host material 124. The host material 124 can be any fluid that dissolves the dyestuff material. Preferably, the host material 124 may be a liquid anisotropic mesogenic material. This includes, but is not limited to, nematic and chiral nematic liquid crystal materials. As will be discussed in further detail, the liquid crystal material assists in providing the polarizing effect. Alternatively, a polymeric liquid crystal material could be used as the fluid host material 124. If precise control of the absorption rate is desired, the optical device may be electrically controlled.

It has been found that by mixing the dyestuff material into a fluid, as defined above, various photochromic properties of the dyestuff are improved. For example, the absorption per concentration of the dyestuff in an anisotropic host material can be improved, therefore, less dye may be needed. This improves the device's transmission of light in its clear or bleached condition. Additionally, less dye material is required, thereby providing a cost savings. Most importantly, the recovery time—the time it takes the material to revert from an absorptive condition to a clear condition—can be reduced from 5–15 minutes to about 2–20 seconds, which is believed to be an attribute of utilizing a fluid host. As used herein, the term "absorbing" is taken to mean reducing the amount of light transmission through the device and/or selectively polarizing components of the light as it passes through the device.

The device 100, in its most simple form, without alignment layers and when the host material 124 is simply a fluid that dissolves the photosensitive or photochromic material 122, functions as previous photochromic glasses. But, by incorporating the material 122 into a fluid host material 124 that imparts orientational properties to the dyestuff material, it has been found that the response time between the transparent and absorptive states is improved by an order of magnitude. This significantly improves the performance and utility of such devices. While not wanting to be bound by theory, it is believed that use of any fluid host material, as opposed to a solid host material, effectively allows the dyestuff material to open and close more quickly at the molecular level when exposed to ultraviolet light.

A nematic liquid crystal material, used as the host material 124, further enhances the performance of the device 100. Moreover, it is possible that the nematic liquid crystal material may itself have photochromic properties. With a liquid crystal material, the device 100, in the absence of a bright ultraviolet light, is essentially transparent to light, regardless of its state of polarization. However, when the device 100 is irradiated with a bright activating or ultraviolet light, as is found in sunlight, it preferentially absorbs at least one polarization component of visible light to substantially reduce the glare that impedes clear vision while also absorbing a portion of the light. Upon removal of the ultraviolet light, the device reverts to its transparent state. As such, the device 100 performs both an anti-glare function and an absorption function. Most importantly, this anti-glare function is performed only in a bright environment when glare presents a problem. This function is passive, inasmuch as no stimulus other than naturally occurring sunlight causes a change in the device's condition between transparent and absorptive.

As best seen in FIG. 2, the mixture of nematic liquid crystal host material 124 and photochromic dyestuff material 122 is aligned essentially parallel with respect to the alignment direction. The long stick shapes represent the liquid crystal molecules and the stick-and-ball shapes represent the dyestuffs, as described in the figure immediately above. The horizontal line represents the propagation direction of a light beam traversing the sample, and the array of arrows on this line represents this light beam being randomly polarized. The arrow on the outgoing side of FIG. 3 shows light that has been linearly polarized by the induced dichroism of the device. Testing has shown that devices of the present invention can have a transmission of greater than 86% and up to 98%, as relative to an ordinary piece of glass. As noted previously, the direction of linear polarization is related to the dyestuff alignments with the liquid crystal material which then depends on the rubbing direction of the alignment layer 116.

Figure 4:
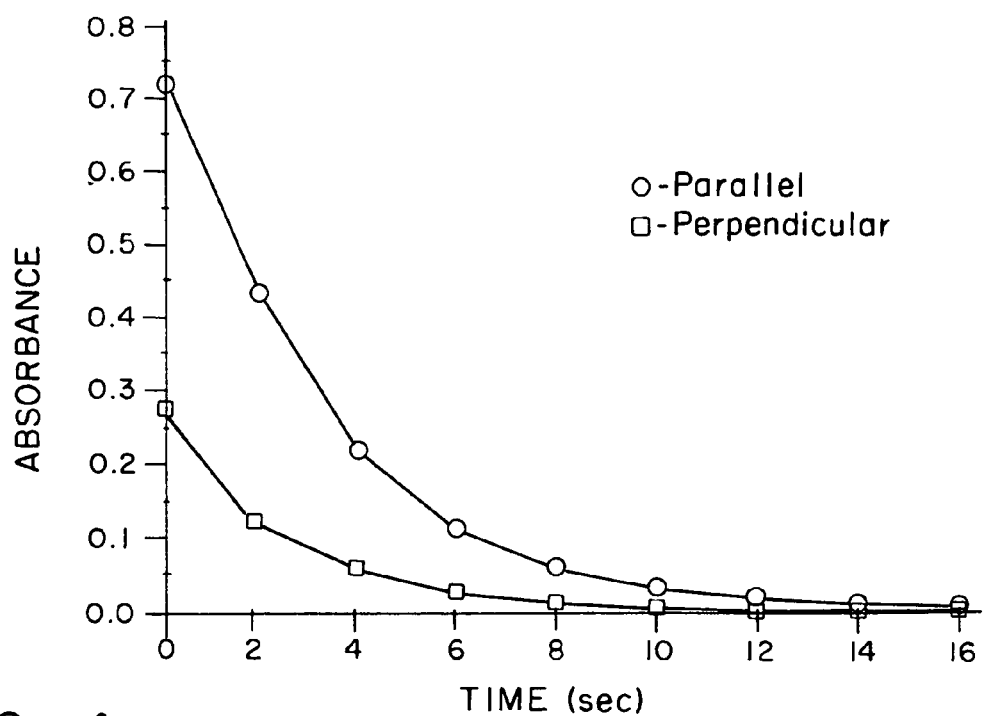
FIG. 4 is a graphical representation of the absorption of the device as a function of time for the two orthogonal polarizations, upon removal of an ultraviolet light source.

In the preferred embodiments of the device 100, the transmissivity to orthogonal components of linearly polarized light, as a function of time, is shown in FIG. 4. The readings associated with the circle data points are representative of light absorption by the device for linearly polarized light with directions of polarization parallel to the direction of the average alignment of the nematic liquid crystal material. The other data readings, indicated by the square data points, are representative of the light absorption by the device for linearly polarized light with a direction perpendicular to the direction of the average alignment of the nematic liquid crystal material. Accordingly, not only does the device 100 exhibit a recovery to the transparent, non-dichroic state after the ultraviolet light is removed, but the recovery happens in only a few seconds. It is submitted that substantial transition from the absorption state to the transparent state is roughly in the same amount of time it takes for one's pupils to dilate after going from a brighter to a dimmer environment. The present invention regains that level of relative transmissivity in as fast as two seconds. Thus, the recovery time of the present invention is about 150 times shorter than attained by the device of the '894 patent. Indeed, the transparent state returns within less than 20 seconds after the activating illumination is removed, many times faster than traditional solid photochromic devices. While not wanting to be bound by theory, it is believed that use of any fluid host material, as opposed to a solid material, effectively allows the dyestuff material to open and close more quickly at the molecular level when exposed to ultraviolet light.

In this embodiment, the main object of the invention is to provide enhanced performance. This enhanced performance is in the form of dramatically shorter response times, as described above, and also in the form of greater photochromic efficiency for a given amount of photochromic dyestuffs. This greater efficiency results from the effective dichroic nature of the dyestuffs, when they are in the activated state. Photochromic dyestuffs, when activated, and when dispersed in a liquid crystalline material, exhibit dichroism. That is, at any given wavelength of light, they exhibit one absorption coefficient ($\alpha_{\parallel}$) for light having polarization direction parallel to the liquid crystal optic axis, and a different absorption coefficient ($\alpha_{\perp}$) than for light having polarization direction perpendicular to the liquid crystal optic axis.

In an isotropic fluid host, the molecules are randomly oriented in space and the effective absorption is a weighted average: $\alpha_{eff}=(2\alpha_{\perp}+\alpha_{\parallel})/3$. In an anisotropic fluid host material, designed for polarization independent operation, the absorption can be increased to $$\alpha_{eff} = \frac{\alpha_{\perp} + \alpha_{\parallel}}{2}$$

or $\alpha_{\perp}$, depending on the desired effect. Thus, this embodiment with an anisotropic host, for the same amount of photochromic dye, can have a greater absorption than the embodiment using an isotropic material. This is particularly important because dyes are typically the most costly components in such a device. Moreover, when the dye is of limited solubility, the amount of dissolved dye is fixed. For both of these reasons, this embodiment is a substantial improvement because it yields greater efficiency for the same amount of dissolved dye. The dyes so far used in this device yield a value $\alpha_{eff}$ that is enhanced by approximately 20%.

In the device 100, one substrate is treated so as to induce the optic axis of the liquid crystal, where it is in contact with that substrate, to lie in the plane parallel to that substrate surface. The other substrate is also treated so as to induce the optic axis of the liquid crystal, where it is in contact with that substrate, to lie not only in the plane parallel to that substrate surface, but also parallel to the direction in which the optic axis of the liquid crystal lies on the other substrate. Thus, the optic axes of the liquid crystal at the location of the two substrates are parallel.

FIG. 3 shows a schematic of this embodiment which is a photo-induced linear dichroic polarizer. That is, when it is excited by activating light, it absorbs light whose polarization direction is parallel to the optic axis of the liquid crystal preferentially over that whose polarization direction is perpendicular to the optic axis of the liquid crystal. In the absence of activating light, it is transparent. Thus, the device, in this embodiment, performs the anti-glare function of the common type of sunglasses referred to in the prior art, yet only performs this function when necessary, that is, in a bright environment where glare presents a problem. The state of polarization preferentially selected depends on the direction in which the substrates are rubbed prior to assembly and/or the absorption axis of the dye molecules. Moreover, the response time of this variation is also significantly improved. It is conceivable that only one substrate could be treated with an alignment layer, or the alignment layers could be rubbed in different directions. However, such variations provide no readily apparent performance advantages other than the improved response time.

EXAMPLE I

A combination of nematic liquid crystals and photochromic dyestuffs was obtained by mixing the nematic liquid crystal material manufactured by MERCK under the trade name E7, with a spiral spyropyran-based dye (Photosol 0265 manufactured by PPG Industries) at a concentration of 0.5 weight percentage dye to liquid crystal. This solution was confined between indium-tin-oxide coated parallel glass plates, separated by a distance of about 24 microns. The glass plates had previously been coated with polyimide coating (sold by DuPont under the trade name PI2555). The coating was applied according to the manufacturer's instructions and then unidirectionally buffed.

Figure 5:
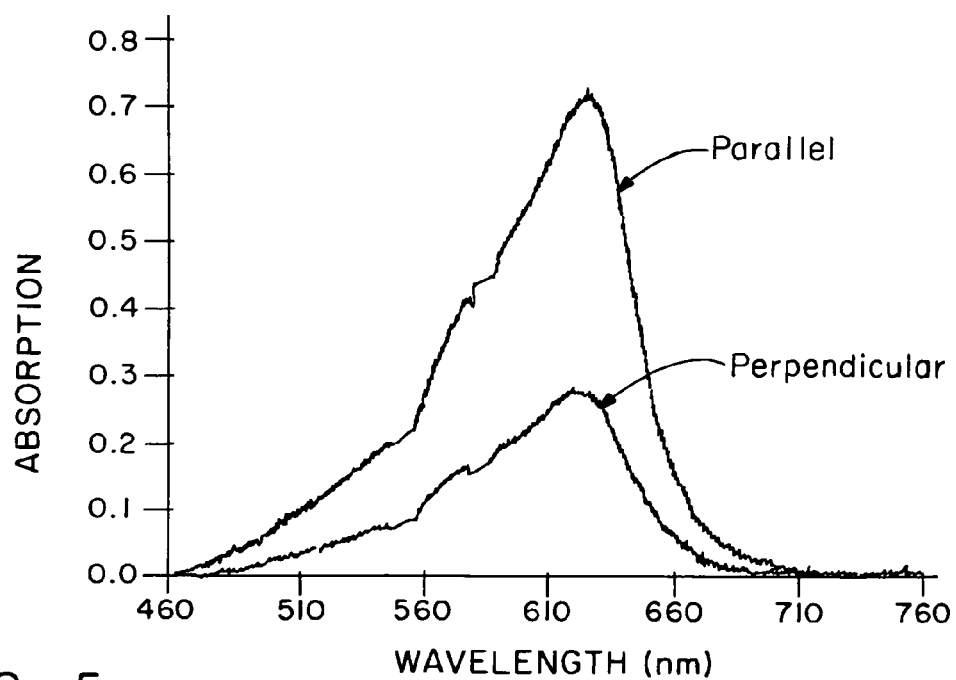
FIG. 5 is a graphical representation of the absorption of the device as a function of wavelength for different polarizations with respect to the average alignment of the mixture.

As best seen in FIG. 5, a graphical representation shows the absorption of light by the device for linearly polarized light with directions of polarization both parallel (the top curve) and perpendicular (the bottom curve) to the direction of average alignment of the nematic liquid crystal material. A skilled artisan will appreciate that these curves reveal a dichroism. In other words, there is a preferred absorption of one polarization state of light over another. FIG. 5 also reveals the absorptive properties of the device after exposure to ultraviolet light having power intensity of about 4 mW/cm$^2$ within the wavelength range of 320–380 nm for about 10 seconds. Bright sunlight has typically 3 mW/cm squared power intensity in this range.

Figure 6:
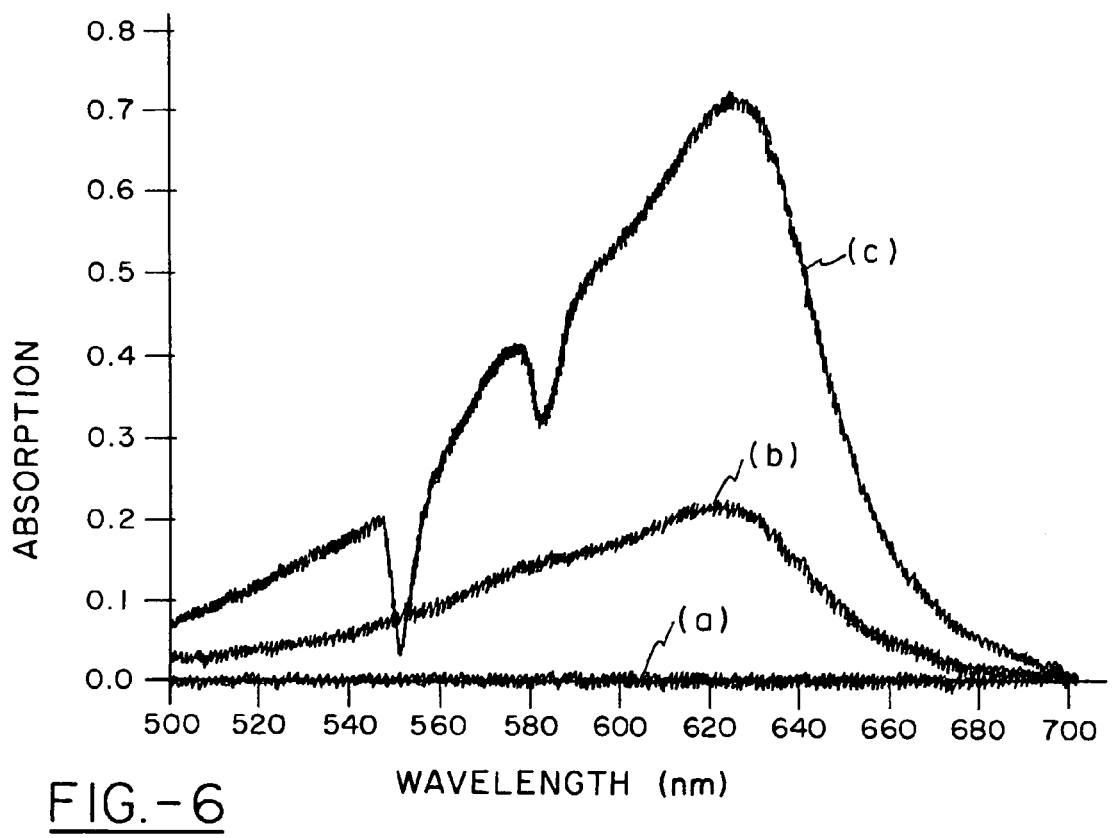
FIG. 6 is a graphical representation of the absorption of the device as a function of wavelength for different exposure times.

As best seen in FIG. 6, the lowest curve, designated by (a), shows the absorption in the absence of ultraviolet light.

The middle curve, designated by (b), shows the absorption only a few seconds after application of the ultraviolet light. Finally, the upper curve, generally designated by (c), shows the absorption about 10 seconds after application of the ultraviolet light. It is noted that the extreme anomalies at approximately 550 nanometers and 580 nanometers are a result of imperfections or artifacts of the measuring device employed and are not properties of the device. Referring back to FIG. 4, it is readily apparent that the disappearance of essentially all absorption as a function of time, by virtue of the removal of the ultraviolet light, has been accomplished. After 15 to 20 seconds, the device is "bleached" so that it no longer absorbs any significant amount of light. Moreover, the difference in the transmittance in the visible region between the two polarizations states in the bleached states is at most 2–3%. Thus, in the bleached state, the device is essentially transparent. The cycle of illuminating with ultraviolet light to induce the dichroism, and then removing the ultraviolet illumination so that the device reverts to the bleached state is repeatable many times with no measurable reduction in performance.

Based upon the foregoing, it will be appreciated that numerous advantages are realized by the foregoing device. With an anisotropic material, the mixture captured between the substrates effectively performs two functions—adjustable absorption and linear polarization—in a single device with much improved transmission that previously were only obtained by distinct and separate devices. Moreover, the present device accomplishes the enhanced absorption and linear polarization utilizing much simpler manufacturing methods and with enhanced performance over previously known devices. Most importantly, with an anisotropic host material, a photo-induced polarizing device can be realized.

Figure 7:
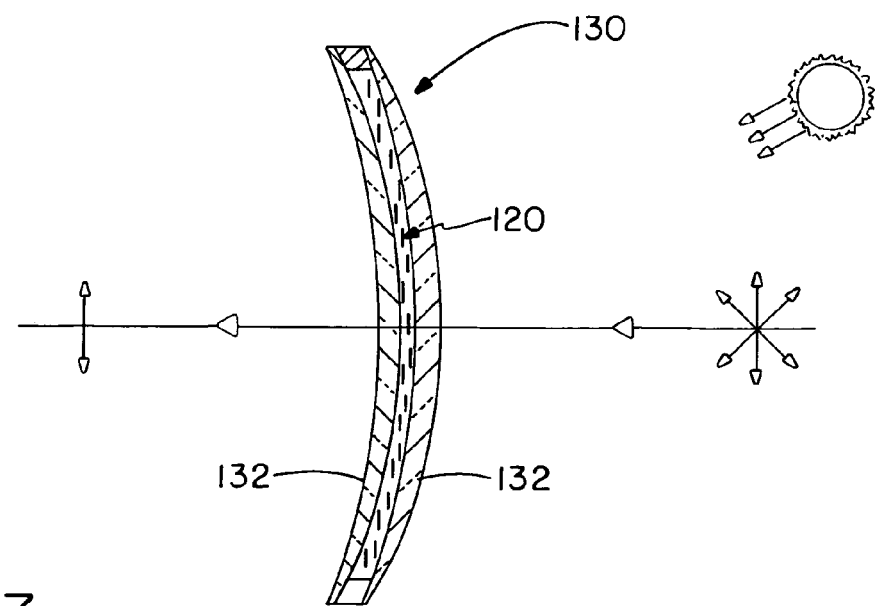
FIG. 7 shows the device utilizing corrective lenses as the substrates.

Use of the device described above may be incorporated into corrective lenses such as shown in FIG. 7. FIG. 7 shows a device, generally designated by the numeral 130, incorporating corrective lenses 132. The device 130 includes the mixture 120 encapsulated between two corrective lenses so as to allow users of corrective lenses to take advantage of the concepts of the present invention. Of course, other types of lenses could be used to capture the mixture 120.

Figure 8:
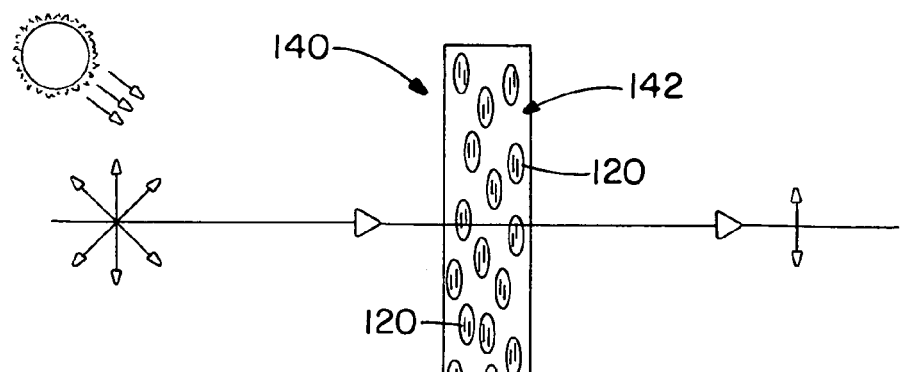
FIG. 8 is a schematic drawing showing the mixture captured within a polymeric film according to the present invention.

Referring now to FIG. 8, the concepts of the present invention may also be incorporated into a film, designated generally by the numeral 140. Use of the film 140 as a carrying medium eliminates the need for substrates and frames as provided by the device 100. The film 140 may be formed by a number of materials and phase separation methods. The film 140 includes a polymer material 142 that has orientational order or contains droplets of the mixture 120 that passes order.

The film can be constructed using a liquid crystal material or a mixture thereof. In one variation, an anisotropic liquid crystal material, such as a nematic polymeric material that can be solidified thermally or by phase separation, and a dyestuff material are used.

In another variation, a solid film of photo-induced dichroic material may be produced in a manner similar to polymer dispersed liquid crystal films. In such an embodiment, the mixture 120 of nematic liquid crystal material and photochromic dyestuff material is dissolved in a transparent polymer, above the polymer's melting temperature. As the polymer mixture cools and hardens, the mixture of nematic liquid crystals and photochromic dyestuffs separates as a distinct fluid phase encapsulated within droplets. This technique is commonly referred to as thermally induced phase separation. As the mixture cools and begins to harden, and when it is cold enough to support itself, but not so cold as to be completely solid, it is drawn into a film. During this process, the film is uniaxially stretched. This stretching aligns the droplets so that the material evidences orientational order and, thus, defines the direction of linear polarization that is preferentially absorbed. Once the film has cooled, the stretched droplet structure is permanently locked into place. With the combination of the mixture so encapsulated, the film 140 exhibits the same photo-induced dichroism as in the embodiment described above. This method of forming the film is advantageous inasmuch as it can be produced in vast quantities and can then later be applied or retrofitted to eyewear or other optical devices.

Figure 9:
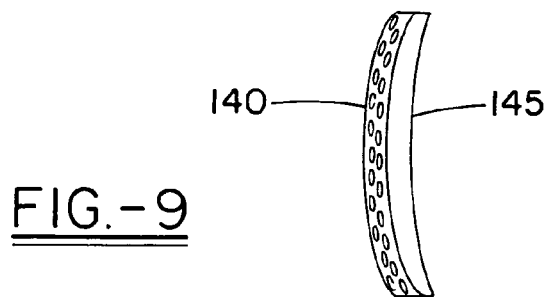
FIG. 9 shows the polymeric film applied to a substrate.

Reference is made to FIG. 9 which shows the film 140 attached by an adhesive or mechanically to a substrate such as a corrective lens 145. Those skilled in the art will also appreciate that other carrying mediums for the mixture 120 may be formed by utilizing solvent-induced phase separation or by polymerization-induced phase separation. It is believed that since the fluid material is encapsulated and/or solidified, the response time between the bleached and darkened states will not be as fast as those embodiments with the dyestuff material in a fluid host material.

Figure 10:
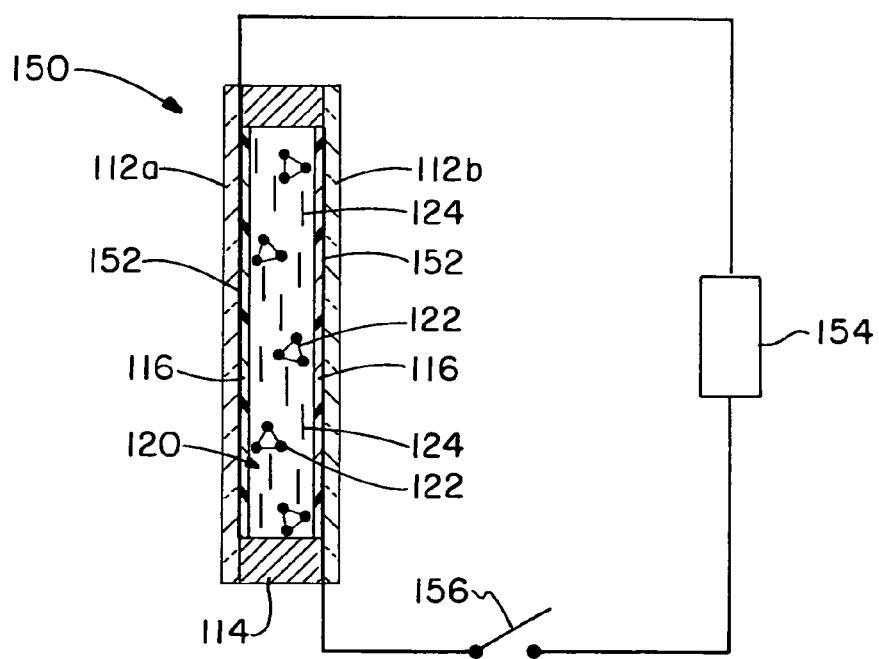
FIG. 10 is a schematic representation of a device that is electrically controlled in an unactivated state.

Referring now to FIG. 10, a device for electrically controlling photo-induced dichroism, made in accordance with the concepts of the present invention, is indicated generally by the numeral 150. The device 150, which may be referred to as an actively controlled device, includes many of the same elements as the device 100 (passive device). The device 150 includes the substrates 112a,b, the frame or sealant 114, alignment layers 116 on one or both substrates 112a, b, and the mixture 120 in any of the variations discussed above. The device 115 also includes electrodes 152 disposed on each substrate, wherein if any alignment layer is used, the alignment layer covers the electrode. A power supply 154 is connected to each electrode to allow for application of an electric potential of variable amplitude and variable frequency across the mixture 120. A switch 156—shown in the open position—may be connected between one of the electrodes 152 and the power supply 154. The switch 156 may be a simple on/off switch or a variable resistor type switch. Use of the power supply 154 allows for active control of the device's variable absorption.

Figure 11:
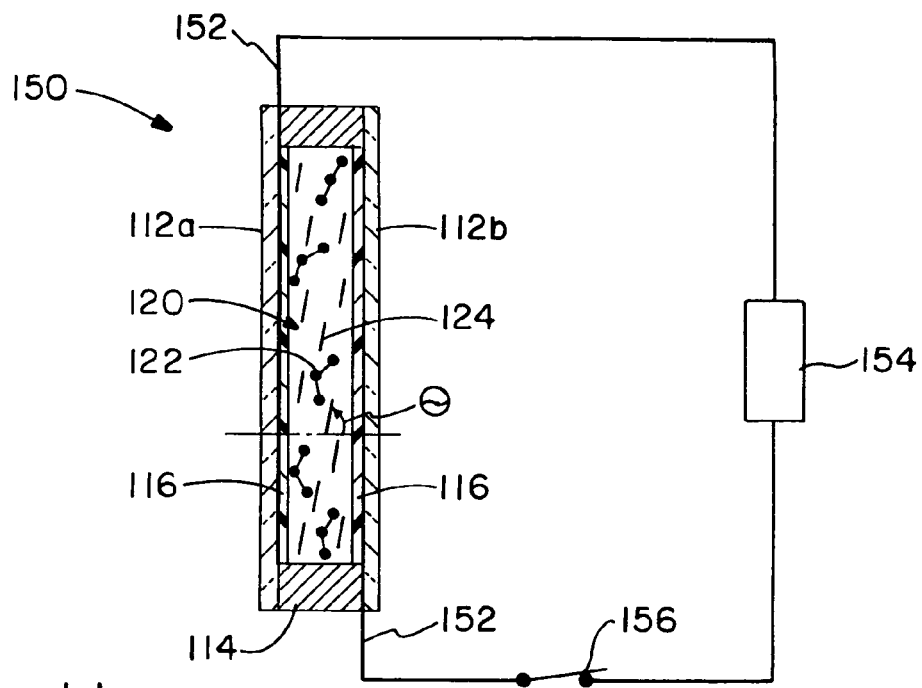
FIG. 11 is a schematic representation of the electrically controlled device in an activated state.

As seen in FIG. 11, with the switch 156 closed, an electric field is applied across the substrates 112a,b. Application of the electric field may be variable and in response to various types of input. Usually, a sensor of some type is associated with the switch to control the amount of electric field applied. For example, the sensor could detect the presence or absence of ambient light or ultraviolet light. In any event, once the electric field is applied, the orientation of the liquid crystal material is altered and the dyestuff material is transformed to absorb the undesirable polarization component(s). The angle θ, which is the angle of the liquid crystal host material, with respect to the substrate, varies according to the strength of the electrical field applied.

Figure 12A:
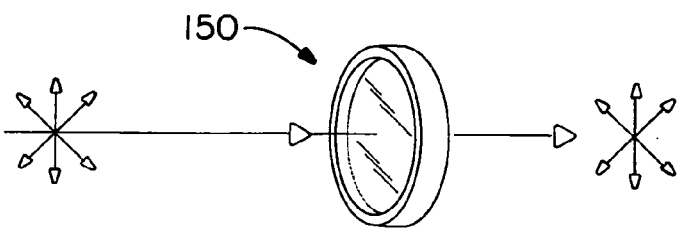
FIGS. 12A–C schematically show the device in various states of operation.
Figure 12B:
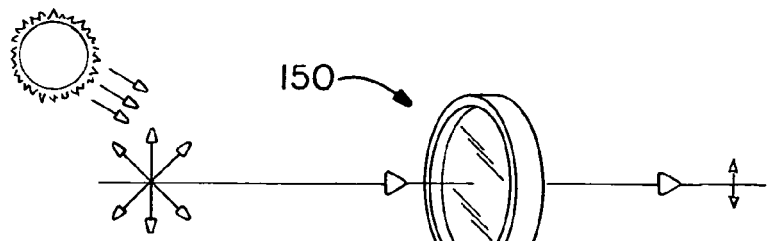
Figure 12C:
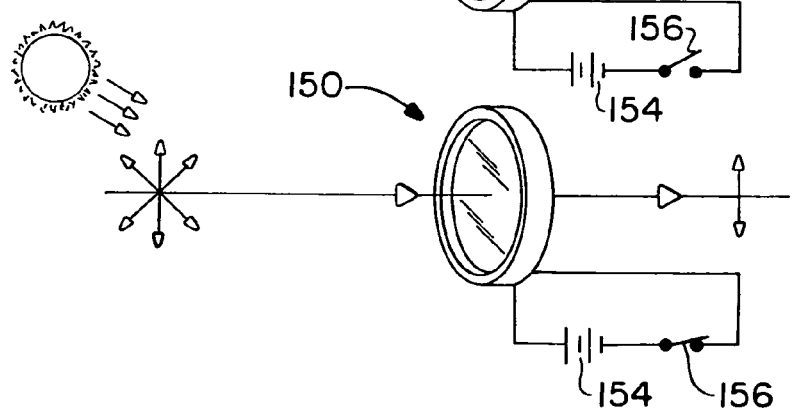

The device 150 has various modes of operation as shown in FIGS. 12A–C. In the absence of bright ultraviolet light (the so-called "bleached" state), as shown in FIG. 12A, the device is essentially transparent.

In FIG. 12B, in the presence of bright ultraviolet light, the device absorbs visible light, i.e., its color changes. When the applied potential difference across the electrodes exceeds a threshold value, the device's absorption decreases substantially, as shown in FIG. 12C. The degree to which the absorption changes can be controlled by varying the amplitude of the applied potential difference. When the applied potential difference is removed, the device quickly reverts to the more absorptive, "colored" state it possessed before the potential difference was applied. In the preferred embodiment, in the presence of ultraviolet light, this device also acts as a dichroic polarizer. The absorption of light is greater for light having its direction of linear polarization parallel to the direction of alignment of liquid crystals on the surface. For this reduction-to-practice, the combination of nematic liquid crystals and photochromic dyestuffs was achieved by mixing the nematic liquid crystal mixture sold by MERCK under trade name E7 with a spyropyran based dye (Photosol 0265 manufactured by PPG) at a concentration of 0.5 wt % dye to liquid crystal.

For the device 150, the alignment coating on the substrates may be chosen to give "homogeneous" alignment of the nematic liquid crystal host. That is, the substrates are treated so that the average direction of molecular orientation of the liquid crystal host is in a fixed direction, parallel to the substrates' surfaces, wherein the nematic liquid crystal host possesses a so-called positive dielectric anisotropy. Furthermore, in the preferred embodiment, a photochromic dye is employed which, when dissolved in an anisotropic host, gives a greater absorption for light polarized parallel to the optic axis.

An alternative embodiment is identical to that above, except a photochromic dye is employed which, when dissolved in an anisotropic host, gives a greater absorption for light polarized perpendicular to the optic axis (negative dichroism). In this embodiment, shown in FIGS. 13A–C, the device is transparent in the bleached state. In the presence of bright ultraviolet light, with no potential difference applied, the device absorbs visible light and polarization component perpendicular to the alignment layer. It preferentially absorbs light with direction of polarization parallel to the alignment direction of the liquid crystal, that is, it acts as a dichroic polarizer. When a potential difference greater than a threshold value is applied to the device, its absorption increases, and its polarizing action (its effective dichroic ratio) decreases.

Another alternative embodiment of the device employs a nematic liquid crystal host with negative dielectric anisotropy. That is, the dielectric constant is smaller for the average direction of molecular orientation parallel to any applied electric field. In this embodiment, shown in FIGS. 14A-B, the alignment coating on the substrates is chosen to give "homeotropic" alignment, in which the average direction of the molecular orientation of the liquid crystal host is perpendicular to the substrates. As in the preferred embodiment, a photochromic dye is employed which, when dissolved in an anisotropic host, gives a greater absorption for light polarized parallel to the optic axis. In this embodiment, the functionality is complementary to that in the preferred embodiment above. In the absence of bright ultraviolet light, the device is essentially transparent. When irradiated with bright ultraviolet light, the device absorbs visible light. When a sufficiently large potential difference is applied across the substrates, the absorption increases; the absorption change is controllable by adjusting the applied potential difference.

An alternative embodiment of the device is one based on the embodiments listed above, but where one or both of the transparent plates are replaced with meniscus lenses to not only provide light transmission control, but also to correct the wearer's vision. A skilled artisan will also appreciate that the degree or amount of polarization can be altered by using different materials and device geometries. In other words, the physical operational parameters of the device may be affected by changes in the cell gap dimension, the alignment layers used, the materials used, and the like.

Thus, it can be seen that the objects of the invention have been satisfied by the structure and its method for use presented above. While in accordance with the Patent Statutes, only the best mode and preferred embodiment has been presented and described in detail, it is to be understood that the invention is not limited thereto or thereby. Accordingly, for an appreciation of true scope and breadth of the invention, reference should be made to the following claims.

What is claimed is:

1. A method for manufacturing a light transmission device, comprising:
    combining a fluid material and a photochromic dyestuff material which exhibits dichroism into a mixture; and
    carrying said mixture in a medium, wherein said mixture varies between a first condition and a second condition, said second condition absorbing and polarizing light upon exposure to any wavelength of ultraviolet light and said mixture relaxing to said first condition, which lets all visible light pass through said mixture, when exposure to any wavelength of ultraviolet light is removed.

2. The method according to claim 1, further comprising:
    providing a pair of opposed substrates having a gap therebetween;
    disposing said mixture into said gap; and
    carrying said pair of opposed substrates in a frame.

3. The method according to claim 2, further comprising:
    disposing an alignment layer on each of said substrates so that said alignment layers face one another.

4. The method according to claim 2, further comprising:
    providing at least one of said substrates as a meniscus lens.

5. The method according to claim 1, further comprising:
    dispersing said mixture through a polymer film; and
    providing a liquid crystal material for said fluid material.

6. The method according to claim 1, further comprising:
    providing a pair of opposed substrates having a gap therebetween;
    disposing an alignment layer on at least one of said substrates facing said gap;
    disposing said mixture into said gap; and
    applying a sealant around said substrates to capture said mixture.

7. The method according to claim 6, further comprising:
    providing a liquid crystal material for said fluid material.

8. The method according to claim 6, further comprising:
    providing a chiral nematic liquid crystal material for said fluid material.

9. The method according to claim 6, further comprising:
    disposing an electrode on each said substrate facing said gap;
    connecting an electric power source to said electrodes; and
    generating an electric field from said electrical power source across said electrodes to control the variation between said first and second conditions even in the presence of any wavelength of ultraviolet light.

10. The method according to claim 9, further comprising:
    generating said electric field, even in the presence of any wavelength of ultraviolet light, to control the orientation of said photochromic dyestuff material.

11. The method according to claim 9, further comprising:
    generating said electric field, even in the presence of any wavelength of ultraviolet light, to force said mixture back toward said first condition.

12. The method according to claim 9, further comprising:
generating said electric field, even in the presence of any wavelength of ultraviolet light, to force said mixture toward said second condition by preferentially absorbing a polarization component.

13. The method according to claim 9, further comprising:
generating said electric field, even in the presence of any wavelength of ultraviolet light, to force said mixture toward said second condition to absorb visible light, but not any polarization component.

14. The method according to claim 5, further comprising:
forming said film by a phase separation process selected from the group consisting of thermally induced, solvent induced, and polymerization induced.

* * * * *